US010259757B2

United States Patent
Liu et al.

(10) Patent No.: US 10,259,757 B2
(45) Date of Patent: Apr. 16, 2019

(54) METHOD FOR STARTING UP A FLUIDIZED CATALYTIC REACTION APPARATUS USED FOR PRODUCING LOWER OLEFINS

(71) Applicant: Dalian Institute of Chemical Physics, Chinese Academy of Sciences, Liaoning Province (CN)

(72) Inventors: Zhongmin Liu, Liaoning Province (CN); Zhihui Lv, Liaoning Province (CN); Changqing He, Liaoning Province (CN); Yu Liu, Liaoning Province (CN); Yue Qi, Liaoning Province (CN); Xiaojian Min, Liaoning Province (CN); Gongwei Wang, Liaoning Province (CN); Xiangao Wang, Liaoning Province (CN); Jinling Zhang, Liaoning Province (CN); Mao Ye, Liaoning Province (CN)

(73) Assignee: Dalian Institute of Chemical Physics, Chinese Academy of Sciences, Liaoning Province (CN)

(*) Notice: Subject to any disclaimer, the term of this patent is extended or adjusted under 35 U.S.C. 154(b) by 0 days.

(21) Appl. No.: 15/936,754

(22) Filed: Mar. 27, 2018

(65) Prior Publication Data

US 2018/0222814 A1 Aug. 9, 2018

Related U.S. Application Data

(63) Continuation-in-part of application No. 14/886,305, filed on Oct. 19, 2015, now abandoned, which is a
(Continued)

(30) Foreign Application Priority Data

Aug. 23, 2006 (CN) .......................... 2006 1 0112558

(51) Int. Cl.
*C07C 1/24* (2006.01)
*B01J 8/26* (2006.01)
(Continued)

(52) U.S. Cl.
CPC ............... *C07C 1/24* (2013.01); *B01J 8/1872* (2013.01); *B01J 8/26* (2013.01); *B01J 29/061* (2013.01);
(Continued)

(58) Field of Classification Search
CPC ....... C07C 1/20; C07C 11/02; C07C 2529/85; C07C 2529/70; B01J 8/008; B01J 8/1872;
(Continued)

(56) References Cited

U.S. PATENT DOCUMENTS

| 2,845,409 A | 7/1958 | Pennington et al. |
| 4,499,327 A | 2/1985 | Kaiser |

(Continued)

FOREIGN PATENT DOCUMENTS

| AU | 2007291793 | 8/2007 |
| AU | 2007291793 B2 | 3/2008 |

(Continued)

OTHER PUBLICATIONS

Intellectual Property Corporation of Malaysia, Malaysian Patent Application No. PI20090203, Substantive Examination Adverse Report, Apr. 15, 2014, pp. 1-3.
(Continued)

*Primary Examiner* — Sharon Pregler
(74) *Attorney, Agent, or Firm* — Hunton Andrews Kurth LLP

(57) ABSTRACT

Disclosed is a method for starting up fluidized reaction apparatus that is used for producing lower olefins from methanol or/and dimethyl ether. Said method includes after heating the catalyst bed of circulating fluidized catalytic
(Continued)

reaction apparatus to above 200° C. or 300° C. by using a starting-up auxiliary heat source, feeding methanol or dimethyl ether raw materials to a reactor, whereby heat released by the reaction makes the temperature of the reaction system apparatus increase quickly to a designed temperature, consequently making the system reach normal operation state rapidly. Said method is suitable for starting up an exothermic fluidized catalytic reaction apparatus and can simplify the apparatus and operation, accordingly lowering the cost.

7 Claims, 2 Drawing Sheets

Related U.S. Application Data continuation-in-part of application No. 12/374,733, filed as application No. PCT/CN2007/002549 on Aug. 23, 2007, now abandoned.

(51) Int. Cl.
| | | |
|---|---|---|
| B01J 38/38 | (2006.01) | |
| B01J 8/18 | (2006.01) | |
| C07C 11/04 | (2006.01) | |
| C07C 11/06 | (2006.01) | |
| B01J 29/06 | (2006.01) | |
| C07C 1/20 | (2006.01) | |

(52) U.S. Cl.
CPC .............. *B01J 38/38* (2013.01); *C07C 1/20* (2013.01); *C07C 11/04* (2013.01); *C07C 11/06* (2013.01); *B01J 2208/00716* (2013.01); *B01J 2229/126* (2013.01); *C07C 2529/06* (2013.01); *C07C 2529/85* (2013.01); *Y02P 20/52* (2015.11); *Y02P 30/42* (2015.11)

(58) Field of Classification Search
CPC .... B01J 8/26; B01J 2008/00716; B01J 29/90; B01J 38/30; B01J 8/0055; B01J 8/1809; B01J 8/1818; C10G 11/185; C10G 2300/4006; C10G 2300/4012; C10G 2300/807; C10G 2400/20; C10G 3/49; C10G 3/57; C10G 3/62; C10G 9/00
See application file for complete search history.

(56) References Cited

U.S. PATENT DOCUMENTS

| 6,143,089 A | 11/2000 | Stephens et al. |
|---|---|---|
| 6,153,089 A | 11/2000 | Das et al. |
| 6,187,983 B1 | 2/2001 | Sun |
| 6,872,867 B1 | 3/2005 | Senetar |
| 2003/0199720 A1 | 10/2003 | Lattner |
| 2005/0038306 A1 | 2/2005 | Beech et al. |
| 2005/0238548 A1 | 10/2005 | van Egmond et al. |
| 2013/0178681 A1* | 7/2013 | Qi ............................ B01J 8/008 585/640 |

FOREIGN PATENT DOCUMENTS

| CN | 1037334 C | 2/1998 |
|---|---|---|
| CN | 1038125 C | 4/1998 |
| CN | 1048429 C | 1/2000 |
| CN | 1065853 C | 5/2001 |
| CN | 1067603 C | 6/2001 |
| CN | 1076219 C | 12/2001 |
| CN | 1656048 A | 8/2005 |
| WO | WO 2006/036293 A1 | 4/2006 |

OTHER PUBLICATIONS

First Examination Report issued by the Government of India Patent Office dated Mar. 22, 2013, pp. 1-2.
Office Action Report in Japanese Appln. No. 2009-524889 dated Jan. 4, 2012, 4 pages.
Office Action Report in Indonesian Appln. No. WO0200900186 dated May 6, 2011, 3 pages.
Ren Jie and Chen Shaozhou; Study on the Regeneration Ability of Zeolite Catalyst for the Alkylation of Benzene with Long Chain Alkene; East China University of Chemical Technology, Shanghai 200237; China Academic Journal Electronic Publishing House, 1994-2010, 5 pages.
International Search Report, PCT Application No. PCT/CN2007/002549, dated Nov. 22, 2007, 3 pages.
Hearing Notice issued by the Indian Patent Office, Indian Patent Application No. 701/DELNP/2009, Jun. 12, 2017, pp. 1-2.
Written Opinion of the First Examination Report by the Brazilian Industrial Property Office, Brazilian Patent Application No. PI0712628-0, dated Mar. 31, 2017, pp. 1-4.

* cited by examiner

METHOD FOR STARTING UP A FLUIDIZED CATALYTIC REACTION APPARATUS USED FOR PRODUCING LOWER OLEFINS

This application is a continuation-in-part of U.S. application Ser. No. 14/886,305, filed Oct. 19, 2015, which is a continuation-in-part of U.S. application Ser. No. 12/374,733 entitled "A Process for Starting up a Fluidized Catalytic Reaction Apparatus Used for Producing Lower Olefins" filed on Jan. 22, 2009, which is a 35 USC § 371 National Phase of International Application No. PCT/CN2007/002549, filed on Aug. 23, 2007 and which claims priority to Chinese Application No. 200610112558.4, filed on Aug. 23, 2006.

FIELD OF THE INVENTION

This invention relates to methods for starting up a fluidized catalytic reaction apparatus used for producing lower olefins from methanol or/and dimethyl ether, which is suitable for the starting up of a circulating fluidized catalytic reaction apparatus of exothermic reaction type, and in particular, for the starting up of a fluidized catalytic reaction apparatus for producing lower olefins such as ethylene, propylene or the like from methanol or/and dimethyl ether.

BACKGROUND

Ethylene and propylene are two basic raw materials with the largest consumption and many applications in chemical industry and are referred to as the stem of the modern organic synthesis industry, and therefore the production technology thereof is the emphasis to be developed competitively by the developed countries. The main route of producing the two olefins is light oil cracking and other methods include the catalytic conversion of lower alcohol ethers, aldehydes, mercaptans, and halohydrocarbons. The impacts of twice petroleum crises in 1970s accelerated the research and developing work of the technology for producing lower olefins through a non-petroleum raw material route wherein the process of methanol conversion has been developed rapidly and shows an enormous commercial application perspective.

Firstly, a process technology for producing lower olefins by taking ZSM-5 zeolite as catalyst and methanol as raw material was provided by Mobile Co., US.

Thereafter, in the middle of 1980s, an assumption of producing lower olefins with a catalyst of a non-zeolite type heteroatom containing aluminum phosphate salt molecular sieve was proposed by Union Carbide Corporation of USA (U.S. Pat. No. 4,499,327).

In 1990, a result of the conversion of methanol to lower olefins high selectively with a catalyst of a SAPO-34 type silicoaluminophosphate molecular sieve having a micropore structure of chabasite was published by Dalian Institute of Chemical Physics, Chinese Academy of Sciences for the first time (Applied Catalysis, 1990, Volume 64, P31-40). Subsequently, a new technology for synthesizing SAPO-34 molecular sieve, a preparation technology of SAPO-34 molecular sieve catalysts and a process technology for producing lower olefins from methanol or/and dimethyl ether were proposed (the patent numbers are CN1037334C, CN1038125C, CN1048429C, CN1065853C, CN1067603C and CN1076219C, respectively), and therefore the production costs of SAPO-34 molecular sieve and the catalyst thereof were reduced substantially, the yields of ethylene and propylene were increased prominently and the economic competitive power of the process technology approached to the level of the petroleum cracking technology.

As stepping into the $21^{st}$ century, in order to cope with the great pressure of scarce petroleum resources and the rapidly increasing oil price, the process technology for producing lower olefins from methanol or/and dimethyl ether using SAPO-34 molecular sieve catalyst developed by the applicant has been capable of satisfying the demand of industrial implementation.

Due to the small pore characteristic of SAPO-34 molecular sieve, this solid acid catalyst tends to be coked quickly and deactivated temporarily in an organic reaction and can be used only after a regeneration by carbon burning. In a continuous industrial production, the continuous stable operation of the small pore molecular sieve such as SAPO-34 or the like can be ensured only when a circulating fluidized apparatus including a reactor and a regenerator is used. In the fluidized apparatus, the temperature of the bed of the reactor for the conversion of methanol or/and dimethyl ether to lower olefins is 400 to 550° C. and the temperature of the catalyst bed of the regenerator is 550 to 700° C. The circulating fluidized apparatus have a very common application in the process of petroleum fluid catalytic cracking (FCC). These apparatus have no heating components themselves and at the stage of starting up, the temperatures of the apparatus are increased depending by the external auxiliary heat-supplying equipment's. In industry, such fluidized apparatus is very large in size and the filled catalyst at starting up is up to hundreds of tons, therefore very large amount of heat is needed to increase the bed temperatures of the reactor and the regenerator of the apparatus to 500° C. or above, and especially when it is over 400° C. or above, it is very difficult to increase the temperature by utilizing external heat.

A method commonly used in the process of FCC is that when the temperature of the regenerator catalyst bed attains 370° C. or above, diesel fuel is spray into the bed and the temperature of the apparatus is elevated using the combustion exothermic reaction of the diesel fuel. The advantage of this method is that it can increase the temperature of the apparatus rapidly and reduce the starting up time greatly. At the same time, FCC is an endothermic reaction and the catalyst is needed to carry heat from the regenerator to maintain the temperature of the catalyst bed, therefore in the actual operation, fuel oil should be sprayed to the regenerator continuously to maintain the temperature of the regenerator.

However, this method has the following disadvantages: (1) a mass of diesel oil is consumed additionally; (2) at the initial stage of spraying oil, as the diesel fuel cannot be burn completely, a mass of carbon black is produced and covered on the catalyst surface, and a part of the carbon black is flowed into the atmosphere with the tail gas and causes pollution to a certain extent; and (3) local superheating may occur so as to make the activity of part of catalyst lost permanently. As the process of the conversion of methanol or/and dimethyl ether to lower olefins is a strong exothermal reaction and the fluidized process of producing lower olefins from methanol or/and dimethyl ether has no precedents in industrial implement, especially SAPO-34 molecular sieve catalyst has not passed the test of actual industrial operation, whether the heating up method of spraying oil in FCC process is feasible or not is still unknown.

Therefore, how to utilize the characteristics of conversion reaction and start up the process is a challenge for this process in industrial implement.

DISCLOSURE OF THE INVENTION

An object of the invention is to provide methods for starting up a fluidized catalytic reaction apparatus used for producing lower olefins from methanol or/and dimethyl ether.

In order to achieve the object described above, in one aspect, the invention provides a method for starting up a fluidized catalytic reaction apparatus for producing lower olefins, wherein said fluidized catalytic reaction apparatus is a circulating fluidized catalytic reaction apparatus comprising a reactor and a regenerator;

wherein the reactor is a dense phase fluidized bed reactor in which is provided with a reactor heat extractor and cyclones, and the regenerator is a dense phase fluidized bed regenerator in which is provided with a regenerator heat extractor and cyclones;

wherein the dense phase fluidized bed reactor is operated under a gauge reaction pressure of 0.05 to 0.3 MPa, a reaction temperature of 420 to 550° C., a dense phase apparent linear speed of 0.3 to 1.5 m/s and a bed layer density of 150 to 600 Kg/m$^3$;

the dense phase fluidized bed regenerator is operated under a gauge reaction pressure of 0.05 to 0.3 MPa, a reaction temperature of 600 to 750° C., a dense phase apparent linear speed of 0.3 to 1.5 m/s and abed layer density of 150 to 600 Kg/m$^3$;

in the reactor heat extractor, cooling water is used as cooling medium, wherein the cooling water is evaporated into steam by absorbing reaction heat, and the reactor heat extractor is a coil heat extractor, U type pipe heat extractor, or a fingertip heat extractor;

in the regenerator heat extractor, cooling water is used as cooling medium, wherein the cooling water is evaporated into steam by absorbing reaction heat, and the regenerator heat extractor is a coil heat extractor, U type pipe heat extractor, or a fingertip heat extractor; and methanol or a mixture of methanol and dimethyl ether is taken as raw material, the method including the steps of:

1) supplying air which has been heated by using a first external auxiliary heat source into the regenerator and introducing nitrogen gas which has been heated by using a second external auxiliary heat source into the reactor, so as to realize the heating of the circulating fluidized apparatus;

2) adding an active catalyst into the reactor become a catalyst bed of the reactor and into the regenerator to become a catalyst bed of the regenerator when the temperatures in the middle parts of the regenerator and the reactor are increased to 200° C. or above, wherein with the addition of the active catalyst, the temperature in the middle part of the reactor is reduced to be 120-180° C. and the temperature in the middle part of the regenerator is reduced to be 120-180° C., 3) adjusting the supply of the heated air into the regenerator and the supply of the heated nitrogen gas into the reactor, while operating the cyclones of the reactor and the regenerator so as to avoid the loss of the active catalyst;

4) heating the catalyst bed of the reactor to a temperature of 200° C. or above by using the heated nitrogen gas, and heating the catalyst bed of the regenerator to a temperature of 300° C. or above by using the heated air;

5) circulating the catalyst between the reactor and regenerator with a circulation rate as low as possible, wherein the catalyst circulation rate is higher than zero and lower than half of the normal catalyst circulation rate, and preferably higher than zero and lower than one fourth of the normal catalyst circulation rate, and most preferably higher than zero and lower than one eighth of the normal catalyst circulation rate, wherein the normal catalyst circulation rate=catalyst loading amount in terms of kilogram in the catalyst bed of the reactor divided by the normal catalyst residence time in the reactor, wherein the normal catalyst residence time is 45 minutes;

6) feeding the raw material to the catalyst bed of the reactor in the fluidized catalytic reaction apparatus, while stopping the introduction of nitrogen gas, whereby the catalyst bed of the reactor is further heated to 350° C. or above, by the heat released by the reaction of the raw material, and, as a consequence of the reaction of the raw material, the coke deposition on the catalyst reaches 0.5% or above; and 7) circulating the catalyst in the reactor with the coke deposition on the catalyst of 0.5% or above to the regeneration bed of the regenerator with a normal catalyst circulation rate, wherein the coke is burn in the regenerator in the presence of air, and thus the temperature of the catalyst bed of the regenerator is increased to 540° C. or above by the heat transported by the circulating catalyst from the reactor, and/or the heat released by the coke being burn in the regenerator; and 8) further increasing the temperature of the catalyst bed of the reactor to 400° C. or above, by the heat released by the reaction of the raw material, and then starting to supply cooling water into the reactor heat extractor and adjusting the supply of the cooling water so as to control the temperature of the catalyst bed layer in the reactor to be stabilized in the range of 420-550° C.; and 9) further increasing the temperature of the catalyst bed of the regenerator to 600° C. or above by the heat released by the coke being burn in the regenerator, and then starting to supply cooling water into the regenerator heat extractor and adjusting the supply of the cooling water so as to control the temperature of the catalyst bed layer in the regenerator to be stabilized in the range of 600-750° C., consequently making the fluidized catalytic reaction apparatus reach normal operation state.

In another aspect, the invention provides a method for starting up a fluidized catalytic reaction apparatus for producing lower olefins, wherein said fluidized catalytic reaction apparatus is a circulating fluidized catalytic reaction apparatus comprising a reactor and a regenerator;

wherein the reactor is a dense phase fluidized bed reactor in which is provided with a reactor heat extractor and cyclones, and the regenerator is a dense phase fluidized bed regenerator in which is provided with a regenerator heat extractor and cyclones;

wherein the dense phase fluidized bed reactor is operated under a gauge reaction pressure of 0.05 to 0.3 MPa, a reaction temperature of 420 to 550° C., a dense phase apparent linear speed of 0.3 to 1.5 m/s and a bed layer density of 150 to 600 Kg/m$^3$;

the dense phase fluidized bed regenerator is operated under a gauge reaction pressure of 0.05 to 0.3 MPa, a reaction temperature of 600 to 750° C., a dense phase apparent linear speed of 0.3 to 1.5 m/s and abed layer density of 150 to 600 Kg/m$^3$;

in the reactor heat extractor, cooling water is used as cooling medium, wherein the cooling water is evaporated into steam by absorbing reaction heat, and the reactor heat extractor is a coil heat extractor, U type pipe heat extractor, or a fingertip heat extractor;

in the regenerator heat extractor, cooling water is used as cooling medium, wherein the cooling water is evaporated into steam by absorbing reaction heat, and the regenerator heat extractor is a coil heat extractor, U type pipe heat extractor, or a fingertip heat extractor; and dimethyl ether is taken as raw material, the method including the steps of:

1) supplying air which has been heated by using a first external auxiliary heat source into the regenerator and introducing nitrogen gas which has been heated by using a second external auxiliary heat source into the reactor, so as to realize the heating of the circulating fluidized apparatus;

2) adding an active catalyst into the reactor become a catalyst bed of the reactor and into the regenerator to become a catalyst bed of the regenerator when the temperatures in the middle parts of the regenerator and the reactor are increased to 200° C. or above, wherein with the addition of the active catalyst, the temperature in the middle part of the reactor is reduced to be 120-180° C. and the temperature in the middle part of the regenerator is reduced to be 120-180° C., 3) adjusting the supply of the heated air into the regenerator and the supply of the heated nitrogen gas into the reactor, while operating the cyclones of the reactor and the regenerator so as to avoid the loss of the active catalyst;

4) heating the catalyst bed of the reactor to a temperature of 300° C. or above by using the heated nitrogen gas, and heating the catalyst bed of the regenerator to a temperature of 300° C. or above by using the heated air;

5) circulating the catalyst between the reactor and regenerator with a circulation rate as low as possible, wherein the catalyst circulation rate is higher than zero and lower than half of the normal catalyst circulation rate, and preferably higher than zero and lower than one fourth of the normal catalyst circulation rate, and most preferably higher than zero and lower than one eighth of the normal catalyst circulation rate, wherein the normal catalyst circulation rate=catalyst loading amount in terms of kilogram in the catalyst bed of the reactor divided by the normal catalyst residence time in the reactor, wherein the normal catalyst residence time is 45 minutes;

6) feeding the raw material to the catalyst bed of the reactor in the fluidized catalytic reaction apparatus, while stopping the introduction of nitrogen gas, whereby the catalyst bed of the reactor is further heated to 350° C. or above, by the heat released by the reaction of the raw material, and, as a consequence of the reaction of the raw material, the coke deposition on the catalyst reaches 0.5% or above; and 7) circulating the catalyst in the reactor with the coke deposition on the catalyst of 0.5% or above to the regeneration bed of the regenerator with a normal catalyst circulation rate, wherein the coke is burn in the regenerator in the presence of air, and thus the temperature of the catalyst bed of the regenerator is increased to 540° C. or above by the heat transported by the circulating catalyst from the reactor, and/or the heat released by the coke being burn in the regenerator; and 8) further increasing the temperature of the catalyst bed of the reactor to 400° C. or above, by the heat released by the reaction of the raw material, and then starting to supply cooling water into the reactor heat extractor and adjusting the supply of the cooling water so as to control the temperature of the catalyst bed layer in the reactor to be stabilized in the range of 420-550° C.; and 9) further increasing the temperature of the catalyst bed of the regenerator to 600° C. or above by the heat released by the coke being burn in the regenerator, and then starting to supply cooling water into the regenerator heat extractor and adjusting the supply of the cooling water so as to control the temperature of the catalyst bed layer in the regenerator to be stabilized in the range of 600-750° C., consequently making the fluidized catalytic reaction apparatus reach normal operation state.

In the described method, the catalyst in the catalyst bed of the reactor is a hydrogen type molecular sieve catalyst.

In the described method, the catalyst in the catalyst bed of the reactor is a solid acid catalyst.

Generally speaking, the invention provides a starting up method for an exothermic reaction type circulating fluidized process for the conversion of methanol or/and dimethyl ether to lower olefins, which can reduce the starting up cost, ensure the long-term stability of various solid acid catalysts, start up the production system rapidly and increase the economic benefits.

The embodiment of the invention is as follows: the reactor in the circulating fluidized catalytic reaction apparatus is heated to 200° C. or above, and the regenerator in the circulating fluidized catalytic reaction apparatus is heated to 300° C. or above, by using a starting up auxiliary heat source, then a circulation of catalyst between the reactor and regenerator is established with a catalyst circulation rate, wherein the catalyst circulation rate is higher than zero and lower than half of the normal catalyst circulation rate, and preferably higher than zero and lower than one fourth of the normal catalyst circulation rate, and most preferably higher than zero and lower than one eighth of the normal catalyst circulation rate, wherein the normal catalyst circulation rate=catalyst loading amount in terms of kilogram in the catalyst bed of the reactor divided by the normal catalyst residence time in the reactor, wherein the normal catalyst residence time is 45 minutes, and then a raw material of methanol or a mixture of methanol and dimethyl ether is fed to the reactor; the heat released by the reaction of the raw material makes the temperature of the reactor increase quickly to a designed temperature and coke on catalyst reach a designed value, thus the induction period of the reaction can be avoided and then the coked catalyst in the reactor is circulated to the regeneration bed of the regenerator with a normal catalyst circulation rate.

The coked catalyst is burned in the regenerator so as to increase the temperature of the regenerator to 540° C. or above rapidly, consequently making the system reach normal operation state rapidly. When dimethyl ether is used as raw material for the reaction, the feeding can be performed only when the reaction apparatus has been heated to be 300° C. or above.

In the embodiments described above, when the temperature of the reactor is between 200 to 300° C., a conversion reaction of methanol ($CH_3OH$) to dimethyl ether ($CH_3OCH_3$) takes place mainly in the catalyst bed and the heat released by the reaction increases the temperature of the reactor. The specific reaction is:

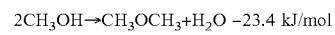
$$2CH_3OH \rightarrow CH_3OCH_3 + H_2O \ -23.4 \text{ kJ/mol}$$

The hydrogen type molecular sieve is a solid acid catalyst and under the effect thereof, the reaction mechanism is:

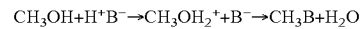
$$CH_3OH + H^+B^- \rightarrow CH_3OH_2^+ + B^- \rightarrow CH_3B + H_2O$$

$$CH_3B + CH_3OH \rightarrow CH_3BCH_3OH \rightarrow CH_3OCH_3 + H^+B^-$$

In this formulae, $B^-$ represents the matrix of the molecular sieve.

After the temperature of the reactor reaches 350° C. or above, the aforementioned conversion reaction of methanol to dimethyl ether and an exothermic conversion reaction of dimethyl ether to olefins ((CH$_2$)$_{2n}$) are taken place:

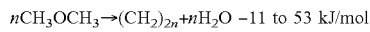
$n$CH$_3$OCH$_3$→(CH$_2$)$_{2n}$+$n$H$_2$O −11 to 53 kJ/mol

When the temperature of the reactor is in between 300° C. and 350° C., an induction period of the reaction may be occurring, wherein the conversion of the raw material is reduced significantly.

The invention has the characteristics described below:

(1) Said fluidized catalytic reaction apparatus is a circulating fluidized catalytic reaction apparatus comprising, consisting essentially of or consisting of a reactor and a regenerator;

wherein the reactor is a dense phase fluidized bed reactor in which is provided with a reactor heat extractor and cyclones, and the regenerator is a dense phase fluidized bed regenerator in which is provided with a regenerator heat extractor and cyclones;

wherein the dense phase fluidized bed reactor is operated under a gauge reaction pressure of 0.05 to 0.3 MPa, a reaction temperature of 420 to 550° C., a dense phase apparent linear speed of 0.3 to 1.5 m/s and a bed layer density of 150 to 600 Kg/m$^3$;

the dense phase fluidized bed regenerator is operated under a gauge reaction pressure of 0.05 to 0.3 MPa, a reaction temperature of 600 to 750° C., a dense phase apparent linear speed of 0.3 to 1.5 m/s and abed layer density of 150 to 600 Kg/m$^3$;

in the reactor heat extractor, cooling water is used as cooling medium, wherein the cooling water is evaporated into steam by absorbing reaction heat, and the reactor heat extractor is a coil heat extractor, U type pipe heat extractor, or a fingertip heat extractor; and in the regenerator heat extractor, cooling water is used as cooling medium, wherein the cooling water is evaporated into steam by absorbing reaction heat, and the regenerator heat extractor is a coil heat extractor, U type pipe heat extractor, or a fingertip heat extractor;

(2) The catalyst is a hydrogen type molecular sieve catalyst or other solid acid catalysts;

(3) When the temperature of the catalyst bed of the reactor reaches 200° C. or above, and the temperature of the regeneration bed of the reactor reaches 300° C. or above, the catalyst starts to circulate between the reactor and regenerator with a catalyst circulation rate, wherein the catalyst circulation rate is higher than zero and lower than half of the normal catalyst circulation rate, and preferably higher than zero and lower than one fourth of the normal catalyst circulation rate, and most preferably higher than zero and lower than one eighth of the normal catalyst circulation rate, wherein the normal catalyst circulation rate=catalyst loading amount in terms of kilogram in the catalyst bed of the reactor divided by the normal catalyst residence time in the reactor, wherein the normal catalyst residence time is 45 minutes.

(5) The raw material of methanol or a mixture of methanol and dimethyl ether is fed to the reactor when the catalyst is circulated between the reactor and regenerator, whereby the catalyst bed of the reactor is further heated to a 350° C. or above, by the heat released by the reaction of the raw material, and, as a consequence of the coke generated in the reaction of the raw material, the coke deposition on the catalyst reaches 0.5%.

(6) Then the coked catalyst in the reactor starts to circulate to a regenerator with a normal catalyst circulation rate, whereby the induction period of the reaction can be avoided.

(7) The reaction of methanol conversion makes the catalyst to be coked, and after the coked catalyst has been entered into the regenerator and when the temperature of the regeneration bed of the regenerator reaches 340° C., the coked catalyst begins to burn and therefore the temperature of the regenerator is increased into a normal operation range rapidly; and (8) By avoiding the use of the manner of heating up the regenerator by spraying diesel fuel to the catalyst bed of the regenerator and burning it, which must be employed at the starting up stage of traditional circulating fluidized catalytic reaction apparatus, this invention can shorten the starting up time and protect the catalyst, reduce the corresponding resource consumption and increase the economic benefits at the same time.

SPECIFIC MODE OF CARRYING OUT THIS INVENTION

Figure 1:
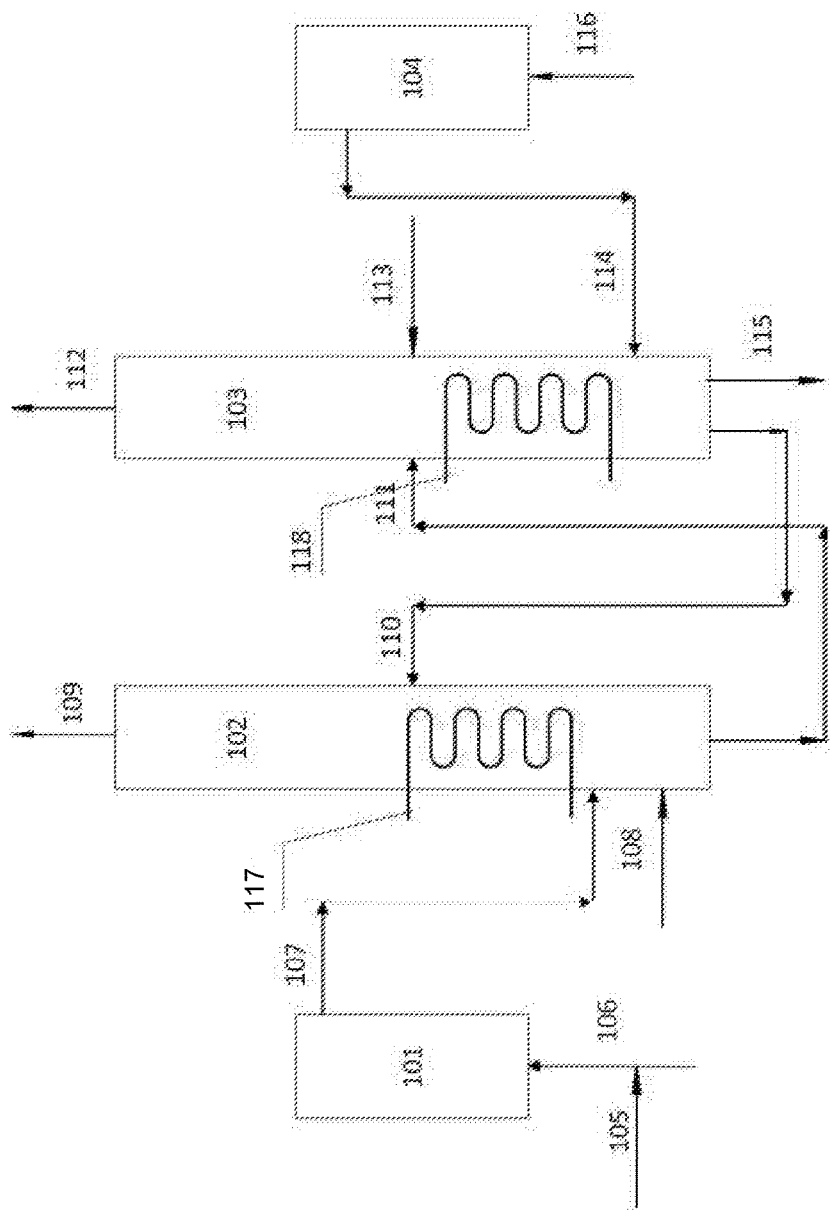
FIG. 1 is the process flow schematic diagram of the reaction-regeneration part in example 1.

After all the apparatuses used in the production system have been detected and confirmed to be in ready states, air is supplied into the regenerator and nitrogen gas is introduced into the reactor. The air and nitrogen gas are heated by using an external auxiliary heat source so as to realize the heating of the circulating fluidized apparatus. When the temperatures in the middle parts of the regenerator and the reactor are increased to 200° C. or above, an active catalyst is added into the apparatus to a predetermined amount. Simultaneously, the amount of nitrogen gas and that of air are adjusted momentarily according to the temperatures of the reactor and the regenerator so as to make the catalyst being circulated between the reactor and the regenerator, and the cyclones of the reactor and the regenerator are insured to be able to work effectively so as to avoid the loss of a mass of catalyst.

When the temperature of the catalyst bed of the reactor is heated to 200° C. and the temperature of the catalyst bed of the regenerator is heated to 300° C. or above, the circulation of the catalyst is controlled to a state as low as possible, wherein the catalyst circulation rate is higher than zero and lower than half of the normal catalyst circulation rate, and preferably higher than zero and lower than one fourth of the normal catalyst circulation rate, and most preferably higher than zero and lower than one eighth of the normal catalyst circulation rate, wherein the normal catalyst circulation rate=catalyst loading amount in terms of kilogram in the catalyst bed of the reactor divided by the normal catalyst residence time in the reactor, wherein the normal catalyst residence time is 45 minutes, and methanol is began to be fed into the reactor to initiate the methanol conversion reaction, and therefore the heat released by the reaction increases the temperature of the catalyst bed of the reactor rapidly. When the temperature of the catalyst bed of the reactor is increased to 450° C., the catalyst circulation rate is increased to stabilize the temperature of the reactor at 450° C., and simultaneously, a coked catalyst with a relatively high temperature is provided to the regenerator to accelerate the heating up of the catalyst bed of the regenerator. When the temperature of the catalyst bed of the regenerator reaches 340° C. or above, the coked catalyst starts burning to accelerate the heating up of the catalyst bed of the regenerator continuously.

When the temperature of the catalyst bed of the generator increases to 540° C. or above and the temperature of the catalyst bed of the reactor increases to a designed temperature, the operation parameters of the heat exchange, the addition of the reaction raw material, the circulation of catalyst and the like are adjusted to stabilize the temperatures of the reactor and the regenerator and the circulation amount of catalyst in designed adequate ranges so as to ensure the complete conversion of the raw material of the reaction and the relatively high selectivity for olefins.

When dimethyl ether is used as raw material, the implement process of the method is substantially the same and the only difference is that the feeding can be performed only when the reaction apparatus has been heated to be 300° C. or above.

The technical characteristics of the invention were introduced below by way of example, but the invention is not limited thereto.

Example 1

FIG. 1 is the process flow schematic diagram of the reaction-regeneration part in this example. 101 is a heater for pre-heating nitrogen gas or steam, 102 is a reactor, 103 is a regenerator, 104 is an auxiliary heater for pre-heating air, 105 is an inlet line for nitrogen gas, 106 is an inlet line for steam, 107 is a line for nitrogen gas or steam to enter the reactor, 108 is a feeding line for methanol, 109 is a line for product gas to a cooling system, 110 is a conveying line for the circulation of the catalyst after regeneration from the regenerator to the reactor, 111 is a conveying line for the circulation of the coked catalyst after reaction from the reactor to the regenerator, 112 is a discharging line for a regenerated fume, 113 is a conveying line for conveying catalyst from a catalyst storage tank to the regenerator, 114 is a line for conveying air from the auxiliary heater to the regenerator, 115 is a conveying line for returning catalyst from the regenerator to the catalyst storage tank, 116 is an inlet line for air, 117 is a reactor heat extractor, and 118 is a regenerator heat extractor.

The dense phase fluidized bed reactor is operated under a gauge reaction pressure of 0.1 MPa, a reaction temperature of 450° C., a dense phase apparent linear speed of 0.8 m/s and a bed layer density of 400 Kg/m$^3$.

The dense phase fluidized bed regenerator is operated under a gauge reaction pressure of 0.1 MPa, a reaction temperature of 650° C., a dense phase apparent linear speed of 0.8 m/s and a bed layer density of 400 Kg/m$^3$.

In the reactor heat extractor, cooling water is used as cooling medium, wherein the cooling water is evaporated into steam by absorbing reaction heat, and the reactor heat extractor is a coil heat extractor, U type pipe heat extractor, or a fingertip heat extractor.

In the regenerator heat extractor, cooling water is used as cooling medium, wherein the cooling water is evaporated into steam by absorbing reaction heat, and the regenerator heat extractor is a coil heat extractor, U type pipe heat extractor, or a fingertip heat extractor.

During the system operation, the total reserve of catalyst in the system was 1.2 to 1.6 times of the treating amount of methanol per hour. Reactor 102 was introduced with nitrogen gas through lines 105, 106, and 107, and the regenerator was introduced with air through lines 116 and 114. Subsequently, the heating apparatus 101 and 104 were started to heat nitrogen and air so that the reactor and regenerator were heated. When the middle part of the regenerator was increased to 502° C., the catalyst conveying apparatus was started and the addition of the catalyst into the regenerator through line 113 was started. During the catalyst addition, the flow rates of nitrogen gas and the air were adjusted momentarily according to the temperature variations of the reactor and the regenerator to make the cyclones of the reactor and the regenerator being capable of working effectively. Simultaneously, the opening degrees of the sliding valves at the bottoms of the reactor and the regenerator were adjusted so as to adjust the circulation amount of the catalyst.

After the addition of catalyst, the temperature of the catalyst bed of the reactor was reduced to be 149° C. and the temperature of the catalyst bed of the regenerator was reduced to be 263° C., and the heating to the reactor and the regenerator were continued. When the temperature of the catalyst bed of the reactor was increased to be 271° C. (the temperature of the bed of the regenerator is also increased to 319° C. accordingly), the catalyst circulation rate between the reactor and the regenerator was controlled to a state as low as possible firstly, and in this specified case, which was one eighth of the normal catalyst circulation rate, and then methanol is fed into the bed of the reactor 102 through line 108 to start the methanol conversion reaction, thereby the reaction was started immediately. The feeding amount of methanol was increased gradually to ensure the complete conversion of methanol.

When the temperature of the catalyst bed of the reactor was 300° C. or lower, the reaction product of methanol was mainly dimethyl ether and the catalyst has a very small coking amount. After the temperature of the bed has been increased to be 300° C. or above, dimethyl ether began to be converted into hydrocarbons and the conversion was increased with the elevation of the temperature, and simultaneously, the coking amount of catalyst was increased continuously. The conversion reactions of methanol to dimethyl ether and further to hydrocarbons were all strong exothermic and therefore the heating up speed of the reactor was accelerated.

When the temperature of the bed of the reactor was increased to 410° C., the temperature of the bed of the regenerator was also increased to be 360° C., the temperature of the catalyst bed of the regenerator was increased rapidly thereafter, that is, at this time, the coke on the coked catalyst began to be burned in air flow automatically. According to the method described above, the temperatures of the catalyst beds of the reactor and the regenerator were increased to be 450° C. and 650° C., respectively, and by adjusting the supply of the cooling water of the reactor heat extractor 117 and the supply of the cooling water of the regenerator heat extractor 118, the temperatures of the reactor and the regenerator were stabilized, wherein the reaction temperature is varied within 450±5° C., while the regeneration temperature is varied within 650±5° C. Simultaneously, the stable operation of the system was realized by stabilizing the circulation amount of the catalyst and controlling the mass space rate of the fed methanol to be 5 h$^{-1}$.

Figure 2:
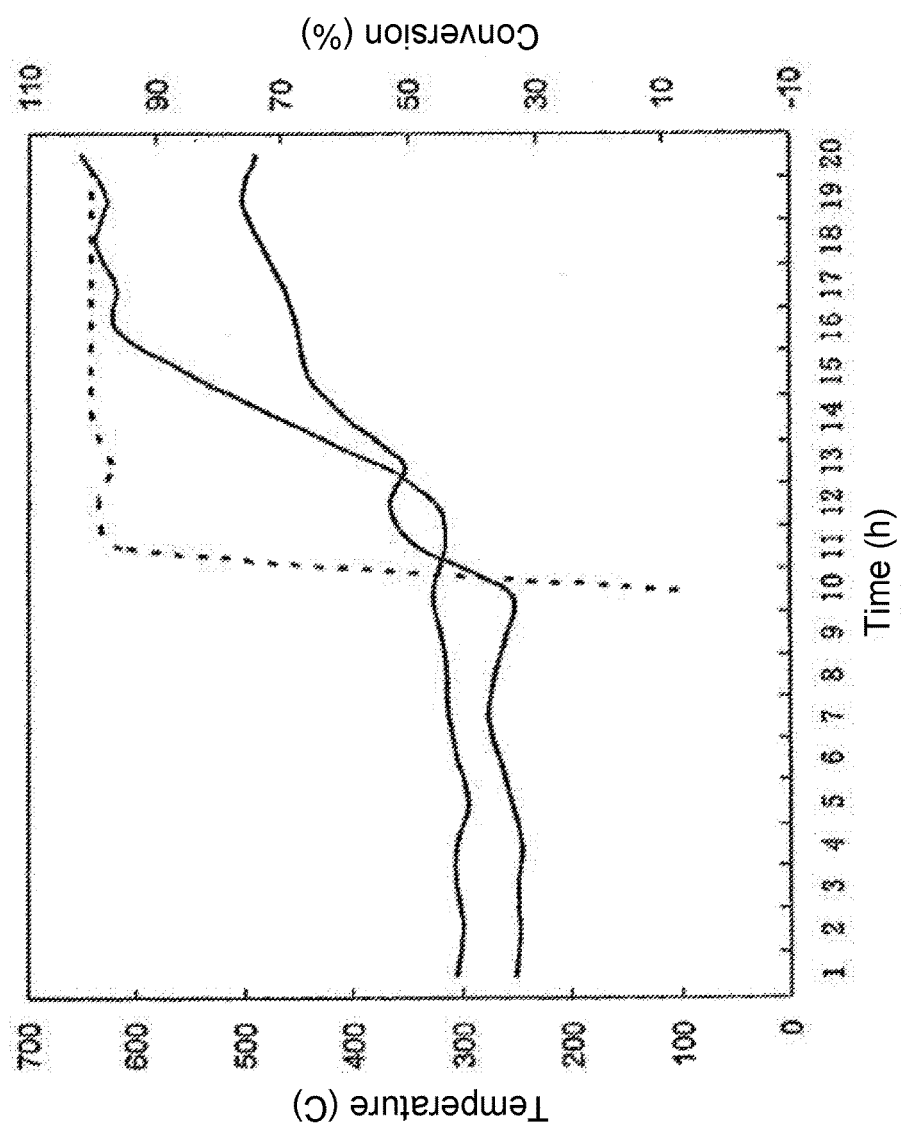
FIG. 2 is the temperature variation curves of the reaction bed and the regeneration bed at the heating up stage of an industrial amplifying apparatus with a methanol treating capacity of 60 tons/day and the variation curve of methanol conversion, according to the method provided in the invention.

FIG. 2 is the temperature variation curves of the reaction bed and the regeneration bed at the heating up stage of an industrial amplifying apparatus with a methanol treating capacity of 60 tons/day and the variation curve of methanol conversion. In FIG. 2, the broken line is the variation curve of methanol conversion and in the two solid lines, the solid line underlying on the left and right sides and superincumbent in the middle part is the temperature variation curve of the reaction bed and the solid line superincumbent on the left and right sides and underlying in the middle part is the temperature variation curve of the regeneration bed.

Example 2

FIG. 1 is the process flow schematic diagram of the reaction-regeneration part in this example. 101 is a heater for pre-heating nitrogen gas or steam, 102 is a reactor, 103 is a regenerator, 104 is an auxiliary heater for pre-heating air, 105 is an inlet line for nitrogen gas, 106 is an inlet line for steam, 107 is a line for nitrogen gas or steam to enter the reactor, 108 is a feeding line for methanol, 109 is a line for product gas to a cooling system, 110 is a conveying line for the circulation of the catalyst after regeneration from the regenerator to the reactor, 111 is a conveying line for the circulation of the coked catalyst after reaction from the reactor to the regenerator, 112 is a discharging line for a regenerated fume, 113 is a conveying line for conveying catalyst from a catalyst storage tank to the regenerator, 114 is a line for conveying air from the auxiliary heater to the regenerator, 115 is a conveying line for returning catalyst from the regenerator to the catalyst storage tank, 116 is an inlet line for air, 117 is a reactor heat extractor, and 118 is a regenerator heat extractor.

The dense phase fluidized bed reactor is operated under a gauge reaction pressure of 0.2 MPa, a reaction temperature of 500° C., a dense phase apparent linear speed of 1.2 m/s and a bed layer density of 200 Kg/m$^3$.

The dense phase fluidized bed regenerator is operated under a gauge reaction pressure of 0.2 MPa, a reaction temperature of 750° C., a dense phase apparent linear speed of 1.2 m/s and a bed layer density of 200 Kg/m$^3$.

In the reactor heat extractor, cooling water is used as cooling medium, wherein the cooling water is evaporated into steam by absorbing reaction heat, and the reactor heat extractor is a coil heat extractor, U type pipe heat extractor, or a fingertip heat extractor.

In the regenerator heat extractor, cooling water is used as cooling medium, wherein the cooling water is evaporated into steam by absorbing reaction heat, and the regenerator heat extractor is a coil heat extractor, U type pipe heat extractor, or a fingertip heat extractor.

During the system operation, the total reserve of catalyst in the system was 1.2 to 1.6 times of the treating amount of methanol per hour. Reactor 102 was introduced with nitrogen gas through lines 105, 106, and 107, and the regenerator was introduced with air through lines 116 and 114. Subsequently, the heating apparatus 101 and 104 were started to heat nitrogen and air so that the reactor and regenerator were heated. When the middle part of the regenerator was increased to 502° C., the catalyst conveying apparatus was started and the addition of the catalyst into the regenerator through line 113 was started. During the catalyst addition, the flow rates of nitrogen gas and the air were adjusted momentarily according to the temperature variations of the reactor and the regenerator to make the cyclones of the reactor and the regenerator being capable of working effectively. Simultaneously, the opening degrees of the sliding valves at the bottoms of the reactor and the regenerator were adjusted so as to adjust the circulation amount of the catalyst.

After the addition of catalyst, the temperature of the catalyst bed of the reactor was reduced to be 149° C. and the temperature of the catalyst bed of the regenerator was reduced to be 263° C., and the heating to the reactor and the regenerator were continued. When the temperature of the catalyst bed of the reactor was increased to be 271° C. (the temperature of the bed of the regenerator is also increased to 319° C. accordingly), the catalyst circulation rate between the reactor and the regenerator was controlled to a state as low as possible firstly, and in this specified case, which was one tenth of the normal catalyst circulation rate, and then methanol is fed into the bed of the reactor 102 through line 108 to start the methanol conversion reaction, thereby the reaction was started immediately. The feeding amount of methanol was increased gradually to ensure the complete conversion of methanol.

When the temperature of the catalyst bed of the reactor was 300° C. or lower, the reaction product of methanol was mainly dimethyl ether and the catalyst has a very small coking amount. After the temperature of the bed has been increased to be 300° C. or above, dimethyl ether began to be converted into hydrocarbons and the conversion was increased with the elevation of the temperature, and simultaneously, the coking amount of catalyst was increased continuously. The conversion reactions of methanol to dimethyl ether and further to hydrocarbons were all strong exothermic and therefore the heating up speed of the reactor was accelerated.

When the temperature of the bed of the reactor was increased to 410° C., the temperature of the bed of the regenerator was also increased to be 360° C., the temperature of the catalyst bed of the regenerator was increased rapidly thereafter, that is, at this time, the coke on the coked catalyst began to be burned in air flow automatically. According to the method described above, the temperatures of the catalyst beds of the reactor and the regenerator were increased to be 500° C. and 750° C., respectively, and by adjusting the supply of the cooling water of the reactor heat extractor 117 and the supply of the cooling water of the regenerator heat extractor 118, the temperatures of the reactor and the regenerator were stabilized, wherein the reaction temperature is varied within 500±5° C., while the regeneration temperature is varied within 750±5° C. Simultaneously, the stable operation of the system was realized by stabilizing the circulation amount of the catalyst and controlling the mass space rate of the fed methanol to be 5 h$^{-1}$.

FIG. 2 is the temperature variation curves of the reaction bed and the regeneration bed at the heating up stage of an industrial amplifying apparatus with a methanol treating capacity of 60 tons/day and the variation curve of methanol conversion. In FIG. 2, the broken line is the variation curve of methanol conversion and in the two solid lines, the solid line underlying on the left and right sides and superincumbent in the middle part is the temperature variation curve of the reaction bed and the solid line superincumbent on the left and right sides and underlying in the middle part is the temperature variation curve of the regeneration bed.

We claim:
1. A method for starting up a fluidized catalytic reaction apparatus for producing lower olefins,
wherein said fluidized catalytic reaction apparatus is a circulating fluidized catalytic reaction apparatus comprising a reactor and a regenerator;
wherein the reactor is a dense phase fluidized bed reactor in which is provided with a reactor heat extractor and cyclones, and the regenerator is a dense phase fluidized bed regenerator in which is provided with a regenerator heat extractor and cyclones;

wherein the dense phase fluidized bed reactor is operated under a gauge reaction pressure of 0.05 to 0.3 MPa, a reaction temperature of 420 to 550° C., a dense phase apparent linear speed of 0.3 to 1.5 m/s and a bed layer density of 150 to 600 Kg/m$^3$;

the dense phase fluidized bed regenerator is operated under a gauge reaction pressure of 0.05 to 0.3 MPa, a reaction temperature of 600 to 750° C., a dense phase apparent linear speed of 0.3 to 1.5 m/s and a bed layer density of 150 to 600 Kg/m$^3$;

in the reactor heat extractor, cooling water is used as cooling medium, wherein the cooling water is evaporated into steam by absorbing reaction heat, and the reactor heat extractor is a coil heat extractor or a fingertip heat extractor;

in the regenerator heat extractor, cooling water is used as cooling medium, wherein the cooling water is evaporated into steam by absorbing reaction heat, and the regenerator heat extractor is a coil heat extractor or a fingertip heat extractor; and methanol or a mixture of methanol and dimethyl ether is taken as raw material, the method including the steps of:

1) supplying air which has been heated by using a first external auxiliary heat source into the regenerator and introducing nitrogen gas which has been heated by using a second external auxiliary heat source into the reactor, so as to realize the heating of the circulating fluidized apparatus;

2) adding an active catalyst into the reactor become a catalyst bed of the reactor and into the regenerator to become a catalyst bed of the regenerator when the temperatures in the middle parts of the regenerator and the reactor are increased to 200° C. or above, wherein with the addition of the active catalyst, the temperature in the middle part of the reactor is reduced to be 120-180° C. and the temperature in the middle part of the regenerator is reduced to be 120-180° C., 3) adjusting the supply of the heated air into the regenerator and the supply of the heated nitrogen gas into the reactor, while operating the cyclones of the reactor and the regenerator so as to avoid the loss of the active catalyst;

4) heating the catalyst bed of the reactor to a temperature of 200° C. or above by using the heated nitrogen gas, and heating the catalyst bed of the regenerator to a temperature of 300° C. or above by using the heated air;

5) circulating the catalyst between the reactor and regenerator with a circulation rate as low as possible, wherein the catalyst circulation rate is higher than zero and lower than half of the normal catalyst circulation rate, wherein the normal catalyst circulation rate=catalyst loading amount in terms of kilogram in the catalyst bed of the reactor divided by the normal catalyst residence time in the reactor, wherein the normal catalyst residence time is 45 minutes;

6) feeding the raw material to the catalyst bed of the reactor in the fluidized catalytic reaction apparatus, while stopping the introduction of nitrogen gas, whereby the catalyst bed of the reactor is further heated to 350° C. or above, by the heat released by the reaction of the raw material, and, as a consequence of the reaction of the raw material, the coke deposition on the catalyst reaches 0.5% or above; and 7) circulating the catalyst in the reactor with the coke deposition on the catalyst of 0.5% or above to the regeneration bed of the regenerator with a normal catalyst circulation rate, wherein the coke is burn in the regenerator in the presence of air, and thus the temperature of the catalyst bed of the regenerator is increased to 540° C. or above by the heat transported by the circulating catalyst from the reactor, and/or the heat released by the coke being burn in the regenerator; and 8) further increasing the temperature of the catalyst bed of the reactor to 400° C. or above, by the heat released by the reaction of the raw material, and then starting to supply cooling water into the reactor heat extractor and adjusting the supply of the cooling water so as to control the temperature of the catalyst bed layer in the reactor to be stabilized in the range of 420-550° C.; and 9) further increasing the temperature of the catalyst bed of the regenerator to 600° C. or above by the heat released by the coke being burn in the regenerator, and then starting to supply cooling water into the regenerator heat extractor and adjusting the supply of the cooling water so as to control the temperature of the catalyst bed layer in the regenerator to be stabilized in the range of 600-750° C., consequently making the fluidized catalytic reaction apparatus reach normal operation state.

2. A method for starting up a fluidized catalytic reaction apparatus for producing lower olefins, wherein said fluidized catalytic reaction apparatus is a circulating fluidized catalytic reaction apparatus comprising a reactor and a regenerator;

wherein the reactor is a dense phase fluidized bed reactor in which is provided with a reactor heat extractor and cyclones, and the regenerator is a dense phase fluidized bed regenerator in which is provided with a regenerator heat extractor and cyclones;

wherein the dense phase fluidized bed reactor is operated under a gauge reaction pressure of 0.05 to 0.3 MPa, a reaction temperature of 420 to 550° C., a dense phase apparent linear speed of 0.3 to 1.5 m/s and a bed layer density of 150 to 600 Kg/m$^3$;

the dense phase fluidized bed regenerator is operated under a gauge reaction pressure of 0.05 to 0.3 MPa, a reaction temperature of 600 to 750° C., a dense phase apparent linear speed of 0.3 to 1.5 m/s and a bed layer density of 150 to 600 Kg/m$^3$;

in the reactor heat extractor, cooling water is used as cooling medium, wherein the cooling water is evaporated into steam by absorbing reaction heat, and the reactor heat extractor is a coil heat extractor or a fingertip heat extractor;

in the regenerator heat extractor, cooling water is used as cooling medium, wherein the cooling water is evaporated into steam by absorbing reaction heat, and the regenerator heat extractor is a coil heat extractor or a fingertip heat extractor; and dimethyl ether is taken as raw material, the method including the steps of:

1) supplying air which has been heated by using a first external auxiliary heat source into the regenerator and introducing nitrogen gas which has been heated by using a second external auxiliary heat source into the reactor, so as to realize the heating of the circulating fluidized apparatus;

2) adding an active catalyst into the reactor become a catalyst bed of the reactor and into the regenerator to become a catalyst bed of the regenerator when the temperatures in the middle parts of the regenerator and the reactor are increased to 200° C. or above, wherein with the addition of the active catalyst, the temperature in the middle part of the reactor is reduced to be 120-180° C. and the temperature in the middle part of the regenerator is reduced to be 120-180° C., 3) adjusting the supply of the heated air into the regenerator and the supply of the heated nitrogen gas into the reactor, while operating the cyclones of the reactor and the regenerator so as to avoid the loss of the active catalyst;

4) heating the catalyst bed of the reactor to a temperature of 300° C. or above by using the heated nitrogen gas, and heating the catalyst bed of the regenerator to a temperature of 300° C. or above by using the heated air;

5) circulating the catalyst between the reactor and regenerator with a circulation rate as low as possible, wherein the catalyst circulation rate is higher than zero and lower than half of the normal catalyst circulation rate, wherein the normal catalyst circulation rate=catalyst loading amount in terms of kilogram in the catalyst bed of the reactor divided by the normal catalyst residence time in the reactor, wherein the normal catalyst residence time is 45 minutes;

6) feeding the raw material to the catalyst bed of the reactor in the fluidized catalytic reaction apparatus, while stopping the introduction of nitrogen gas, whereby the catalyst bed of the reactor is further heated to 350° C. or above, by the heat released by the reaction of the raw material, and, as a consequence of the reaction of the raw material, the coke deposition on the catalyst reaches 0.5% or above; and 7) circulating the catalyst in the reactor with the coke deposition on the catalyst of 0.5% or above to the regeneration bed of the regenerator with a normal catalyst circulation rate, wherein the coke is burn in the regenerator in the presence of air, and thus the temperature of the catalyst bed of the regenerator is increased to 540° C. or above by the heat transported by the circulating catalyst from the reactor, and/or the heat released by the coke being burn in the regenerator; and 8) further increasing the temperature of the catalyst bed of the reactor to 400° C. or above, by the heat released by the reaction of the raw material, and then starting to supply cooling water into the reactor heat extractor and adjusting the supply of the cooling water so as to control the temperature of the catalyst bed layer in the reactor to be stabilized in the range of 420-550° C.; and 9) further increasing the temperature of the catalyst bed of the regenerator to 600° C. or above by the heat released by the coke being burn in the regenerator, and then starting to supply cooling water into the regenerator heat extractor and adjusting the supply of the cooling water so as to control the temperature of the catalyst bed layer in the regenerator to be stabilized in the range of 600-750° C., consequently making the fluidized catalytic reaction apparatus reach normal operation state.

3. The method as claimed in claim 1 or 2, characterized in that the reaction apparatus is a circulating fluidized catalytic reaction apparatus consisting of a reactor and a regenerator.

4. The method as claimed in claim 1 or 2, characterized in that the catalyst in the catalyst bed of the reactor is a hydrogen type molecular sieve catalyst.

5. The method as claimed in claim 1 or 2, characterized in that the catalyst in the catalyst bed of the reactor is a solid acid catalyst.

6. The method as claimed in claim 1 or 2, characterized in that the catalyst circulation rate is lower than one fourth of the normal catalyst circulation rate.

7. The method as claimed in claim 1 or 2, characterized in that the catalyst circulation rate is lower than one eighth of the normal catalyst circulation rate.

* * * * *